US006894176B2

(12) United States Patent
Dotson et al.

(10) Patent No.: US 6,894,176 B2
(45) Date of Patent: *May 17, 2005

(54) REACTION PRODUCT MIXTURES INCLUDING BOTH SYMMETRIC COMPOUNDS AND ASYMMETRIC DIPOLAR MULTI-SUBSTITUTED ALDITOL DERIVATIVES

(75) Inventors: Darin L. Dotson, Spartanburg, SC (US); Brian M. Burkhart, Greenville, SC (US); John D. Anderson, Moore, SC (US); Jeffrey R. Jones, Inman, SC (US); Shawn R. Sheppard, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 116 days.

This patent is subject to a terminal disclaimer.

(21) Appl. No.: 10/286,217

(22) Filed: Nov. 1, 2002

(65) Prior Publication Data

US 2003/0120092 A1 Jun. 26, 2003

Related U.S. Application Data

(62) Division of application No. 09/815,485, filed on Mar. 23, 2001, now Pat. No. 6,555,696.

(51) Int. Cl.[7] .................... C07D 323/04; C07D 319/14; C08K 5/1575; C08K 5/159
(52) U.S. Cl. ...................... 549/364; 549/363; 524/108; 252/401; 252/405; 252/407
(58) Field of Search ........................ 524/108; 252/401, 252/405, 407; 549/364, 363

(56) References Cited

U.S. PATENT DOCUMENTS

| | | | |
|---|---|---|---|
| 3,201,363 A | 8/1965 | Spurlin et al. | 260/30.4 |
| 3,207,736 A | 9/1965 | Wijga et al. | 260/93.7 |
| 3,234,233 A | 2/1966 | Bolger et al. | 260/326 |
| 3,320,267 A | 5/1967 | Poos et al. | 260/295 |
| 3,367,926 A | 2/1968 | Voeks et al. | 260/93.5 |
| 3,527,736 A | 9/1970 | Averink et al. | 260/78.4 |
| 3,721,682 A | 3/1973 | Murai et al. | 260/340.7 |
| 3,793,401 A | 2/1974 | Nield et al. | 260/876 |
| 3,829,450 A | 8/1974 | Schmerling et al. | 260/346.3 |
| 3,873,643 A | 3/1975 | Wu et al. | 260/878 |
| 3,882,194 A | 5/1975 | Krebaum et al. | 260/878 |
| 3,928,687 A | 12/1975 | Wada et al. | 428/461 |
| 3,933,779 A | 1/1976 | Baron et al. | 260/93.5 |
| 3,941,746 A | 3/1976 | Stephen et al. | 260/45.8 |
| 3,954,913 A | 5/1976 | Uebele et al. | 260/880 |
| 4,016,118 A | 4/1977 | Hamada et al. | 260/17.4 SG |
| 4,039,491 A | 8/1977 | Ikeda et al. | 260/875 |
| 4,134,895 A | 1/1979 | Roth et al. | 260/326 |
| 4,134,927 A | 1/1979 | Tomoshige et al. | 260/878 |
| 4,154,816 A | 5/1979 | Roehl et al. | 424/68 |
| 4,371,645 A | 2/1983 | Mahaffey, Jr. | 524/108 |

(Continued)

FOREIGN PATENT DOCUMENTS

| | | | |
|---|---|---|---|
| DE | 1 544 851 | 5/1970 | C08F/29/02 |
| DE | 1 694 914 B | 3/1972 | C08F/29/02 |
| EP | 0267 695 | 5/1988 | C08K/5/00 |
| EP | 0336 573 | 3/1989 | C08K/5/00 |
| FR | 2 075 549 | 9/1971 | C08F/45/00 |
| FR | 2 656 620 | 7/1991 | C08L/23/02 |
| GB | 2 290 296 | 12/1995 | C08K/5/3412 |
| JP | 53-40760 | 4/1978 | 548/435 |
| JP | 57-18682 | 1/1982 | |
| JP | 58-160343 | 9/1983 | C08L/67/20 |
| JP | 60-13837 | of 1985 | |
| JP | 61-17834 | 5/1986 | |
| JP | 01-180514 | 7/1989 | G02C/7/02 |
| JP | 1990-59832 | 12/1990 | |
| JP | 03-076815 A | 4/1991 | D01F/8/06 |
| JP | 05-139460 | 6/1993 | B65D/77/00 |
| JP | 07-173342 | 7/1995 | C08L/23/10 |
| JP | 1995-286066 | 10/1995 | |
| WO | 92/19221 | 11/1992 | |

OTHER PUBLICATIONS

H.N. Beck, "Heterogeneous Nucleating Agents of Polypropylene Crystallization", Journal of Applied Polymer Science, vol. 11, pp. 673–685, 1967.

Overman et al., "An Annual Publication of Satisfactory Methods for the Preparation of Organic Chemicals." Organic Synthesis, vol. 71, pp. 48–55, 1993.

Snider et al., "Mn(III)–Based Oxidative Free Radical Cyclization of Unsaturated Ketones," Journal of Organic Chemistry, vol. 60, pp. 5376–5377, 1995.

Fillon et al., "Self–Nucleation and Recrystallization of Isotactic Polypropylene (alpha Phase) Investigated by Differential Scanning Calorimetry," Journal of Polymer Science: Part B: Polymer Physics, vol. 31, pp. 1383–1393, 1993.

Fillon et al., "Self–Nucleation and Enhanced Nucleation of Polymers. Definition of a Convenient Calorimetric "Efficiency Scale" and Evaluation of Nucleating Additives in Isotactic Polypropylene (alpha phase)," Journal of Polymer Science: Part B: Polymer Physics, vol. 31 pp. 1395–1504, 1993.

*Primary Examiner*—Joseph D. Anthony
(74) *Attorney, Agent, or Firm*—Terry T. Moyer; John E. Vick, Jr.

(57) ABSTRACT

Certain multi-substituted dibenzylidene sorbitol acetals having electron withdrawing groups as constituents and electron donating groups on the other such that the compounds are asymmetric in structure and are dipolar in nature are provided. Polymer compositions comprising such compounds, are also contemplated which may be utilized within, as merely examples, food or cosmetic containers and packaging. These inventive asymmetric dipolar dibenzylidene sorbitol acetals are also useful as gelling agents for water and organic solvents, particularly those used in the preparation of antiperspirant gel sticks.

2 Claims, No Drawings

U.S. PATENT DOCUMENTS

| | | | |
|---|---|---|---|
| 4,452,942 A | 6/1984 | Shida et al. | 525/74 |
| 4,476,184 A | 10/1984 | Lubowitz et al. | 428/288 |
| 4,503,219 A | 3/1985 | Reffert et al. | 528/481 |
| 4,518,582 A | 5/1985 | Schamper et al. | 424/66 |
| 4,704,421 A | 11/1987 | Teskin et al. | 524/287 |
| 4,739,017 A | 4/1988 | Tabor et al. | 525/300 |
| 4,743,444 A | 5/1988 | McCall | 424/65 |
| 4,778,837 A | 10/1988 | Waterman et al. | 524/89 |
| 4,781,917 A | 11/1988 | Luebbe et al. | 424/65 |
| 4,801,637 A | 1/1989 | McCullough et al. | 524/287 |
| 4,808,650 A | 2/1989 | Titus et al. | 524/108 |
| 4,816,261 A | 3/1989 | Luebbe et al. | 424/65 |
| 4,829,114 A | 5/1989 | Trotoir et al. | 524/243 |
| 4,902,807 A | 2/1990 | Kobayashi et al. | 549/364 |
| 4,996,334 A | 2/1991 | Kaitoh et al. | 549/364 |
| 5,013,778 A | 5/1991 | Bath et al. | 524/173 |
| 5,015,684 A | 5/1991 | Kobayashi et al. | 524/108 |
| 5,049,605 A | 9/1991 | Rekers | 524/108 |
| 5,106,999 A | 4/1992 | Gardlik et al. | 549/364 |
| 5,135,975 A | 8/1992 | Rekers et al. | 524/108 |
| 5,456,725 A * | 10/1995 | Bruhnke | 8/403 |
| 5,470,898 A | 11/1995 | Syed | 524/84 |
| 5,491,187 A | 2/1996 | Ward et al. | 524/159 |
| 5,574,174 A | 11/1996 | Syed | 549/364 |
| 5,609,855 A | 3/1997 | Oh et al. | 424/65 |
| 5,696,186 A | 12/1997 | Videau | 524/48 |
| 5,731,474 A | 3/1998 | Scrivens et al. | 568/592 |
| 5,922,793 A | 7/1999 | Amos et al. | 524/159 |
| 5,929,146 A | 7/1999 | Amos et al. | 524/89 |
| 6,096,811 A | 8/2000 | Amos et al. | 524/89 |
| 6,495,620 B1 * | 12/2002 | Jones et al. | 524/108 |
| 6,548,581 B2 * | 4/2003 | Anderson et al. | 524/108 |
| 6,555,696 B2 * | 4/2003 | Dotson et al. | 549/364 |
| 6,593,427 B2 * | 7/2003 | Kobayashi et al. | 525/194 |
| 2002/0137953 A1 * | 9/2002 | Lever et al. | 549/453 |

* cited by examiner

REACTION PRODUCT MIXTURES INCLUDING BOTH SYMMETRIC COMPOUNDS AND ASYMMETRIC DIPOLAR MULTI-SUBSTITUTED ALDITOL DERIVATIVES

CROSS REFERENCE TO RELATED APPLICATIONS

This application is a divisional of application Ser. No. 09/815,485 filed Mar. 23, 2001, which granted Apr. 29, 2003 as U.S. Pat. No. 6,555,696 on.

FIELD OF THE INVENTION

This invention relates to plastic additives which are useful as nucleating agents and which are especially useful for improving the optical properties of polymeric materials. More particularly, this invention relates to certain multi-substituted dibenzylidene sorbitol acetals having both electron withdrawing and electron donating groups such that the compounds are asymmetric in structure and thus dipolar in nature. Polymer compositions comprising such compounds are also contemplated which may be utilized within, as merely examples, food or cosmetic containers and packaging. These inventive asymmetric dipolar dibenzylidene sorbitol acetals are also useful as gelling agents for water and organic solvents, particularly those used in the preparation of antiperspirant gel sticks.

BACKGROUND OF THE PRIOR ART

All U.S. Patents cited below are herein entirely incorporated by reference.

Numerous attempts have been made to improve the clarity and physical properties of polyolefins through the incorporation of certain kinds of additives. Certain applications require good clarity or transparency characteristics. These include certain types of plastic plates, sheets, films, containers, and syringes that need to exhibit clarity primarily to facilitate identification of articles, etc., stored, wrapped, and/or covered therewith. Such commercially available plastic additives fall into two categories termed "melt sensitive" and "melt insensitive". Melt sensitive additives possess melting points below or near the normal processing temperatures of polyolefin-based resins and include dibenzylidene sorbitol (DBS) systems. Melt insensitive additives do not melt at normal processing temperatures and include sodium benzoate and salts of organic phosphates as examples.

U.S. Pat. No 4,016,118 to Hamada, et al. teaches that a polyolefin plastic composition containing 0.1% to 0.7% dibenzylidene sorbitol (DBS) as an additive will show improved transparency and reduced molding shrinkage over compositions containing a substituted benzoic acid salt. Additional advancements in sorbitol-based clarification technology have been driven by the need for improved transparency, reduction of plate-out during processing, and improved organoleptic properties (e.g., odor, taste, etc.). In order to overcome these deficiencies, many derivatives of DBS in which the aromatic rings are substituted with various groups have been proposed.

Mahaffey, in U.S. Pat. No. 4,371,645 discloses a series of dibenzylidene sorbitols having the general formula:

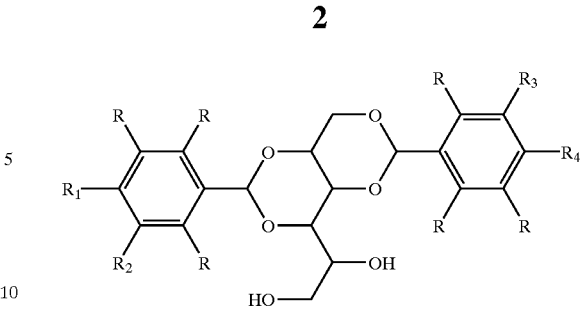

wherein R, $R_1$, $R_2$, $R_3$, and $R_4$, are selected from hydrogen, lower alkyl, hydroxy, methoxy, mono- and di-alkylamino, amino, nitro, and halogen, with the proviso that at least one of $R_1$, $R_2$, $R_3$, and $R_4$ is chlorine or bromine. Effective concentrations of the disclosed substituted DBS derivatives range from 0.01 to about 2 percent by weight of the total composition weight. Further improvements in transparency characteristics are disclosed by Titus, et al. in U.S. Pat. No. 4,808,650. In this patent mono and disubstituted DBS derivatives having the formula:

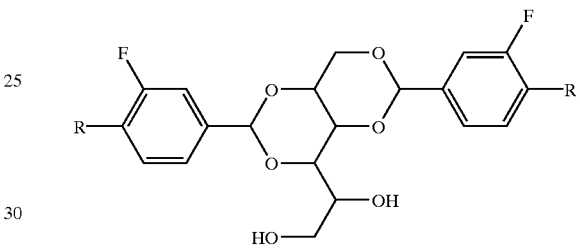

in which R may be hydrogen or fluorine provide improved clarity applications in polyolefins. Rekers, in U.S. Pat. No. 5,049,605 discloses a series of dibenzylidene sorbitols having the general formula:

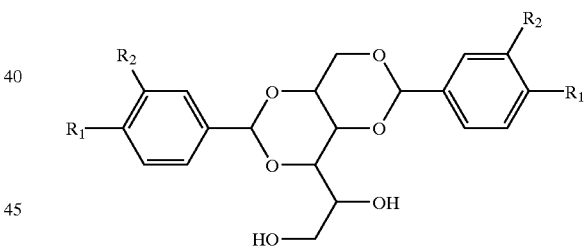

in which $R_1$ and $R_2$ are independently selected from lower alkyl groups containing 1–4 carbons which can also form a carbocyclic ring containing up to 5 carbon atoms. Also disclosed are polyolefin plastics containing the above group of dibenzylidene sorbitols. Videau, in U.S. Pat. No. 5,696,186 discloses substituted DBS derivatives with an alkyl group (methyl, ethyl, or the like) or halogen (fluorine, chlorine, or the like) on the benzene rings for use as nucleation/clarification agents in polyolefins.

Dibenzylidene sorbitol (DBS) is a well known gelling agent for a variety solvent systems as disclosed in U.S. Pat. No. 4,154,816, Roehl et al.; U.S. Pat. No. 4,816,261, Luebbe et al.; and U.S. Pat. No. 4,743,444 to McCall. U.S. Pat. No. 5,609,855 to Oh et al. and PCT Patent Application WO/92/19221 to Juneja et al. disclose that di(meta-fluorobenzylidene) sorbitol and di(meta-chlorobenzylidene) sorbitol are extremely useful as gelling agents in the preparation of antiperspirant gel sticks. These two respective DBS systems form effective hard gels and show improved gel stability in the acidic environment of antiperspirant formulations.

DETAILED DESCRIPTION OF THE INVENTION

According to the present invention, a polyolefin plastic composition having improved transparency is provided which comprises a polymer selected from aliphatic polyolefins and copolymers containing at least one aliphatic olefin and one or more ethylenically unsaturated comonomers and at least one di-acetal of an alditol (such as sorbitol, xylitol, and ribitol) conforming to the following structure (I):

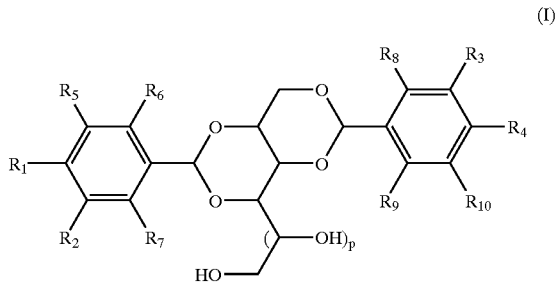

(I)

wherein p is 0 or 1, $R_5$, $R_6$, $R_7$, $R_8$, $R_9$, and $R_{10}$ are each the same or different and are selected from electron donating groups, such as hydrogen, lower alkyl groups containing 1–4 carbon atoms, lower alkoxy groups, and electron withdrawing groups, such as halogens (meaning fluorine, chlorine, bromine, and iodine); $R_1$, $R_2$, $R_3$, and $R_4$ are the same or different and are selected from electron donating groups, such as hydrogen, lower alkyl groups containing 1–4 carbon atoms, lower alkoxy groups, or any two are combined to form a carbocyclic or methylenedioxy ring, and electron withdrawing groups, such as nitro and halogens; with the first proviso that if one of said $R_1$, $R_2$, $R_3$, or $R_4$ groups is nitro, then no other nitro groups are present anywhere on the compound; with a second proviso that at least at least two electron withdrawing groups (other than the nitro group, above) must be present and must be present as either the pair of $R_1$ and $R_2$ or the pair of $R_3$ and $R_4$ such that if one pair comprises such electron withdrawing groups, the other pair must comprise electron donating groups and the same ring system comprising such electron donating groups must not comprise any electron withdrawing groups. Preferably, the electron donating group-containing ring (and electron withdrawing group-containing ring) must be 3,4-disubstituted with such groups, although such a limitation is not required. Such inventive compounds (and not just the polyolefin compositions comprising such compounds) are also encompassed individually and in combination within the scope of this invention, particularly in its broadest sense an asymmetric alditol di-acetal comprising at least two arylidene components wherein one of said arylidene components possesses either a single nitro pendant group or at least two electron drawing pendant groups and the other arylidene component must comprise at least two electron donating pendant groups.

It should be appreciated with regard to the structural formula set forth above that while only the 1,3:2,4 isomer is represented, this structure is provided for convenience only and the invention is not limited to only isomers of the 1,3:2,4 type, but may include any and all other isomers as well so long as the compound contains two benzylidene acetal substitutents on the alditol moiety.

The preferred diacetals of the present invention are condensation products of sorbitol and at least two substituted benzaldehydes (or arylaldehydes). Examples of suitable substituted reactants include 3,4-dichlorobenzaldehyde, 3,4-dimethylbenzaldehyde, 3,4-difluorobenzaldehyde, 3,4-diethylbenzaldehyde, 2,4-dichlorobenzaldehyde, 2,4-difluorobenzaldehyde, 2,4-dimethylbenzaldehyde, 3,4-diethylbenzaldehyde, 3-nitrobenzaldehyde, 4-nitrobenzaldehyde, 3,4-dimethoxybenzaldehyde, 2,4-dimethoxybenzaldehyde, 3,4-diethoxybenzaldehyde, 2,4-diethoxybenzaldehyde, 6-formyltetralin, 5-formylindan, 3,4-methylenedioxybenzaldehyde (piperonal), and the like. Non-limiting preferred diacetals of the present invention thus include 1,3-O-(3,4-dichlorobenzylidene):2,4-O-(3,4-dimethylbenzylidene) sorbitol, 1,3-O-(3,4-dimethylbenzylidene):2,4-O-(3,4-dichlorobenzylidene) sorbitol, 1,3-O-(3,4-difluorobenzylidene):2,4-O-(3,4-dimethylbenzylidene) sorbitol, , 1,3-O-(3,4-dimethylbenzylidene):2,4-O-(3,4-difluorobenzylidene) sorbitol, 1,3-O-(3,4-dichlorobenzylidene):2,4-O-(3,4-dimethoxybenzylidene) sorbitol, 1,3-O-(3,4-dimethoxybenzylidene):2,4-O-(3,4-dichlorobenzylidene) sorbitol, 1,3-O-(3,4-dichlorobenzylidene):2,4-O-(5-indanylidene) sorbitol, 1,3-O-(5-indanylidene):2,4-O-(3,4-dichlorobenzylidene) sorbitol, 1,3-O-(4-nitrobenzylidene):2,4-O-(3,4-dimethylbenzylidene) sorbitol, 1,3-O-(3,4-dimethylbenzylidene):2,4-O-(4-nitrobenzylidene) sorbitol, 1,3-O-(4-nitrobenzylidene):2,4-O-(3,4-methylenedioxybenzylidene) sorbitol, 1,3-O-(3,4-methylenedioxybenzylidene):2,4-O-(4-nitrobenzylidene) sorbitol, 1,3-O-(3,4-dichlorobenzylidene):2,4-O-(3,4-dimethylbenzylidene) xylitol, and 1,3-O-(3,4-dimethylbenzylidene):2,4-O-(3,4-dichlorobenzylidene) xylitol.

The compositions of the present invention also include solvent gels containing 0.2% to 10% of the above diacetals as a gelling agent. Solvents useful herein include, as merely examples, lower monohydric alcohols, polyhydric alcohols, and mixtures thereof. Water may also be included as a portion of the solvent. However, the solvent will generally comprise water at levels no greater than 5% by weight of the final composition. Examples of solvents which may be utilized in the present invention include liquid polyethylene glycols (e.g., diethylene glycol, triethylene glycol), liquid polypropylene glycols (e.g., dipropylene glycol, tripropylene glycol), liquid polypropylene polyethylene glycol copolymers, ethanol, n-propanol, n-butanol, t-butanol, 2-methoxyethanol, 2-ethoxyethanol, ethylene glycol, 1,2-propylene glycol, 1,3-propylene glycol, 1,4-butylene glycol, 1,2-butylene glycol, isopropanol, isobutanol, diethylene glycol monomethyl ether, diethylene glycol monoethylether, 1,3-butylene glycol, 2,3-butylene glycol, 2,4-dihydroxy-2-methylpentane, trimethylene glycol, glycerine, 1,3-butanediol, 1,4-butanediol, and the like, and mixtures thereof. As used herein, polyethylene glycols, polypropylene glycols, and polypropylene polyethylene glycol copolymers include alkyl ether derivatives of these compounds (e.g., ethyl, propyl, and butyl ether derivatives). Examples of such compounds are butyl ether derivatives of polypropylene polyethylene glycol copolymers, such as PPG-5-buteth-7.

These solvents are fully described, for example, in U.S. Pat. No. 4,518,582 to Schamper et al. and European Published Application 107,330 to Luebbe et al. incorporated herein by reference. The preferred solvents for use herein include liquid polyethylene glycols, liquid polypropylene glycols, liquid polypropylene polyethylene glycol copolymers, propylene glycol, 1,3-butylene glycol, and 2,4-dihydroxy-2-methylpentane (sometimes referred to as hexylene glycol), and mixtures thereof. Particularly preferred solvents include propylene glycol, dipropylene glycol, tripropylene glycol, triethylene glycol, hexylene glycol, and mixtures thereof.

Other organic solvents useful herein include aromatics, halogenated aromatics, nitrated aromatics, ketones, amines, nitriles, esters, aldehydes, and mixtures thereof. Examples of solvents which may be utilized in the present invention include xylenes (o-, m-, and p-substituted), 2-chlorotoluene, fluorobenzene, nitrobenzene, benzonitrile, dimethylsulfoxide (DMSO), N,N-dimethylformamide (DMF), and 1-methyl-2-pyrrolidinone (NMP).

The diacetals of the present invention may be prepared by the reaction of one mole of sorbitol with about 1 mole each of two different benzaldehydes in the presence of an acid catalyst. The temperature employed in the reaction will vary widely depending upon the characteristics, such as melting points or boiling points, of the benzaldehydes employed as a starting material in the reaction. The reaction medium may be an aqueous medium or a non-aqueous medium. One very advantageous method that can be employed to prepare diacetals of the invention is similar to that described in U.S. Pat. No. 3,721,682, to Murai et al. (New Japan Chemical Company Limited), the disclosure of which is hereby incorporated herein by reference. While the disclosure of the patent is limited to dibenzylidene sorbitols, it has been found that the diacetals of the present invention may also be conveniently prepared by the method described therein. Additional methods for preparing DBS systems can be found in U.S. Pat. No. 5,731,474 to Scrivens et al., U.S. Pat. No. 4,902,807 to Kobayashi et al. which discloses DBS having an alkyl group or halogen for use as clarifying agents, and U.S. Pat. No. 5,106,999 to Gardlik et al. which discloses the preparation of di(meta-fluorobenzylidene) sorbitol, di(meta-chlorobenzylidene) sorbitol, and di(meta-bromobenzylidene) sorbitol.

It is important to note that the reaction necessary to produce the desired asymmetric diacetals requires the utilization of different benzaldehyde reactants. In such a reaction, invariably four different diacetal compounds can be produced. For instance, Example 1 below shows the production of a mixture of 1,3-O-(3,4-dichlorobenzylidene):2,4-O-(3,4-dimethylbenzylidene) sorbitol, 1,3-O-(3,4-dimethylbenzylidene):2,4-O-(3,4-dichlorobenzylidene) sorbitol, 1,3:2,4-bis(3,4-dimethylbenzylidene) sorbitol, and 1,3:2,4-bis(3,4-dichlorobenzylidene) sorbitol simultaneously. Due to the similar solubilities of such DBS compounds (in each instance, not just Example 1), it has been found to be extremely difficult to separate these individual compounds from the reaction product mixture. Such a mixture thus not only includes the desired inventive asymmetric compound or compounds, but such a mixture is an inventive composition as well. Hence, the terms "diacetal compositions", as well as "reaction product mixtures" (as well as their singular forms) are intended to encompass such an inventive mixture including the desired asymmetries.

In order to produce such diacetal compositions (and thus the inventive asymmetric compounds themselves), the starting materials must include the desired alditol (such as sorbitol), and at least two different benzaldehydes. Generally, as noted above, the molar ratio of alditol to benzaldehyde reactant is at least 1:2 for diacetal formation. In this specific situation of producing asymmetric compounds, the same general molar ratio is followed (with the ability to use more or less of either type of reactant if desired); however, the benzaldehyde component is measured as a total amount of the at least two different benzaldehyde reactant compounds necessary for asymmetric production. Thus, the benzaldehyde component is split into at least two different measurements of the individual reactants utilized. Such a split of amounts can be as disparate as a range of from 1:25 to 25:1 of molar ratios of benzaldehydes, if desired. More likely, and more desired, however, is a range of from 1:5 to 5:1, preferably from 1:4 to 4:1, more preferably from 1:3 to 3:1, still more preferably from 1:2 to 2:1, and most preferably a molar ratio of substantially 1:1.

Although such general methods can be followed, it has been unexpectedly and surprisingly found that the combination of two different aldehydes (with different pendant groups attached thereto), especially with one benzaldehyde possessing electron donating groups in the 3,4-position and the other possessing electron withdrawing groups in the 3,4-position (except 3- and 4-nitrobenzaldehyde), as described above, react in such a manner as to produce a non-statistical yield of a majority of asymmetric diacetal compounds. Theoretically, a total yield relatively close to a 25% individual yield of the four possible products from such a reaction is expected [thus 25% of the symmetrical 3,4-dimethyldibenzylidene sorbitol, 25% of the symmetrical 3,4-dichlorodibenzylidene sorbitol, and 25% each of the asymmetric products of 1,3-O-(3,4-dichlorobenzylidene):2,4-O-(3,4-dimethylbenzylidene) sorbitol and 1,3-O-(3,4-dimethylbenzylidene):2,4-O-(3,4-dichlorobenzylidene) sorbitol]. However, as noted in the specific example above, the resultant product mixture has an appreciable majority (about 63% by weight) of the dipolar asymmetric diacetals. The remaining products are present, but in much lower proportions as compared to their theoretical yields. Although such a result is not readily understood, without intending to be limited to any specific scientific theory, it is believed that such a phenomenon results due to the stability accorded the above-noted asymmetric compounds.

Furthermore, it has been determined that such dipolar asymmetric compounds provide excellent clarifying properties to polyolefin compositions (such as, preferably polypropylene). In fact, the haze characteristics of polypropylene articles clarified therewith have measured at levels below about 6%. Again, without intending to be limited to any specific scientific theory, it is believed that such excellent clarity results are provided by the substantially uniform orientation of these asymmetric diacetals within the target polypropylene itself.

It appears that, upon an initial production of a molten composition of polyolefin and clarifying agent, during the subsequent cooling to produce a solid article the clarifying agents form a fibrous network at high temperatures, on which the polypropylene recrystallizes at lower temperatures. The more uniform orientation of such a fibrous network, seemingly the more uniform orientation of crystallized polymer within the final solid article. With one end of the clarifying compound exhibiting a strong ability to withdraw electrons, and the other much weaker in such a respect or, more importantly, exhibiting a capacity to donate electrons, it has been theorized that the stronger withdrawing end will most likely attract (or be attracted to) the end of compound exhibiting electron donating abilities. Thus, within the molten polymer, it is believed that such an arrangement occurs readily, thereby providing a substantially uniform arrangement within the necessary fibrous network for recrystallization of the target polymer. In such an instance, although some non-asymmetric compounds are present, it has been found that purification of the desired uniform asymmetric compound is highly desired, although it is not required to provide a clarifying agent that ultimately provides a desirable low haze characteristics within the final solid polyolefin article. Of course, preferably a pure formulation of asymmetric alone (and only one type of asymmetric, as two will be produced) is highly desired, although rather difficult to produce due to problems associated with the requisite separation procedures from the other three reaction products.

The inventive sorbitol diacetals prepared by the above techniques may contain a minor or even a major portion of by-product monoacetal and triacetal as impurities (in addition to the aforementioned expected reaction product mixture of diacetals). Although it may not always be necessary to remove these impurities prior to incorporation of the diacetal into the polyolefin, it may be desirable to do so and such purification may serve to enhance the transparency of the resin produced thereby. Purification of the diacetal may be accomplished, for instance, by removal of the triacetal impurities by the extraction thereof with a relatively non-polar solvent. By removal of the impurities, the product may be purified so that the amount of diacetal in the additive composition contains, preferably, though not necessarily, at least about 90 percent and even up to 95 percent of the diacetal composition or more.

The proportion of diacetal in the composition of this invention is an amount sufficient to improve the transparency of the composition, generally from about 0.01 to about 2 percent by weight, preferably about 0.1 to about 1 percent by weight, based upon the total weight of the composition may be provided. When the content of the diacetal composition is less than about 0.01 percent by weight, the resulting composition may not be sufficiently improved in respect to transparency characteristics. When the content of diacetal composition is increased beyond about 2 percent by weight, no additional advantage can be observed.

The polyolefin polymers of the present invention may include aliphatic polyolefins and copolymers made from at least one aliphatic olefin and one or more ethylenically unsaturated comonomers. Generally, the comonomers, if present, constitute a minor amount, e.g., about 10 percent or less or even about 5 percent or less, of the entire polyolefin, based upon the total weight of the polyolefin. Such comonomers may serve to assist in clarity improvement of the polyolefin, or they may function to improve other properties of the polymer. Examples include acrylic acid and vinyl acetate, etc. Examples of olefin polymers whose transparency can be improved conveniently according to the present invention are polymers and copolymers of aliphatic monoolefins containing 2 to about 6 carbon atoms which have an average molecular weight of from about 10,000 to about 2,000,000, preferably from about 30,000 to about 300,000, such as polyethylene, linear low density polyethylene, polypropylene, crystalline ethylenepropylene copolymer, poly(1-butene), vinyl cyclohexane, 1-hexene, 1-octene, and polymethylpentene. The polyolefins of the present invention may be described as basically linear, regular polymers that may optionally contain side chains such as are found, for instance, in conventional, low density polyethylene.

Other polymers that may benefit from the nucleation and clarification properties of the sorbitol acetals of the present invention include polyethylene terephthalate, polybutylene terephthalate, and polyamides, among others.

The olefin polymer or copolymer used in the composition of the present invention is crystalline, and the diffraction of light caused by microcrystals contained in it is considered to be responsible for the deterioration of the transparency of the polymer. It is thought that the diacetal composition functions in the target polyolefin to reduce the size of the microcrystals thereby improving the transparency of the polymer.

The composition of the present invention can be obtained by adding a specific amount of the diacetal composition directly to the olefin polymer or copolymer, and mixing them by any suitable means. Alternatively, a concentrate containing as much as about 20 percent by weight of the diacetal composition in a polyolefin masterbatch may be prepared and be subsequently mixed with the resin. Furthermore, the inventive alditol derivatives (and other additives) may be present in any type of standard polyolefin additive form, including, without limitation, powder, prill, agglomerate, liquid suspension, and the like, particularly comprising dispersion aids such as polyolefin (e.g., polyethylene) waxes, stearate esters of glycerin, montan waxes, mineral oil, and the like. Basically, any form may be exhibited by such a combination or composition including such combination made from blending, agglomeration, compaction, and/or extrusion.

Other additives such as a transparent coloring agent or plasticizers (e.g., dioctyl phthalate, dibutyl phthalate, dioctyl sebacate, mineral oil, or dioctyl adipate), can be added to the composition of the present invention so long as they do not adversely affect the improvement of transparency of the product. It has been found that plasticizers such as those exemplified above may in fact aid in the improvement of the transparency by the diacetal composition.

With regard to other additives it may also be desirable to employ the diacetal compositions disclosed above in combination with other conventional additives having known transparency improving effects such as, for instance, para-t-butylbenzoic acid, its salts, low molecular weight waxy polypropylene and the like. It may even be desirable to provide the particular diacetal compositions of the present invention in the polyolefin composition in combination with the previously described dibenzylidene sorbitol additive disclosed in U.S. Pat. Nos. 4,016,118 to Hamada et al., 5,049,605 to Rekers, and the like. In such applications, generally at least about 10 percent, preferably about 25 percent, or even about 50 percent or more of the clarity improving component will be the diacetal compositions of the present invention, with the remainder being comprised of other known clarifying agents, plasticizers, etc.

The compositions of the present invention may be obtained by adding the multi-substituted dipolar asymmetric benzylidene sorbitol acetals to the polymer or copolymer and merely mixing the resultant composition by any suitable means. The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

Other additives may also be used in the composition of the present invention, provided they do not interfere with the primary benefits of the invention. It may even be advantageous to premix these additives or similar structures with the nucleating agent in order to reduce its melting point and thereby enhance dispersion and distribution during melt processing. Such additives are well known to those skilled in the art, and include plasticizers, lubricants, catalyst neutralizers, antioxidants, light stabilizers, colorants, other nucleating agents, and the like. Some of these additives may provide further beneficial property enhancements, including improved aesthetics, easier processing, and improved stability to processing or end use conditions.

In particular, it is contemplated that certain organoleptic improvement additives be added for the purpose of reducing the migration of degraded benzaldehydes from reaching the surface of the desired article. The term "organoleptic improvement additive" is intended to encompass such compounds and formulations as antioxidants (to prevent degradation of both the polyolefin and possibly the target alditol derivatives present within such polyolefin), acid neutralizers (to prevent the ability of appreciable amounts of residual acids from attacking the alditol derivatives), and benzaldehyde scavengers (such as hydrazides, hydrazines, and the like, to prevent the migration of foul tasting and smelling benzaldehydes to the target polyolefin surface). Such compounds and formulations can be added in any amounts in order to provide such organoleptic improvements as needed. However, the amounts should not appreciably affect the haze results for the target polyolefin itself. Thus, lower amounts on the order of from about 20 ppm to about 2,000 ppm of the total polyolefin component are desired.

The compositions of the present invention are suitable as additives to improve the clarity of packaging materials and container materials for cosmetics, food-stuffs, and the like, because they give film, sheet, and other fabricated articles excellent transparency and physical properties.

PREFERRED EMBODIMENTS OF THE INVENTION

The following examples further illustrate the present invention but are not to be construed as limiting the invention as defined in the claims appended hereto. All parts and percents given in these examples are by weight unless otherwise indicated.

Dipolar Asymmetric Compound Formation

EXAMPLE 1

Preparation of Asymmetric 3,4-Dichloro/3,4-Dimethyl DBS

A one liter four-necked cylindrical shaped reaction flask equipped with a Dean-Stark trap, condenser, thermometer, nitrogen inlet, and a mechanical stirrer was charged with 42.00g of sorbitol (0.2306 mole), 700 mL of cyclohexane, 3,4-dichlorobenzaldehyde (40 g, 0.2306 moles), 3,4-dimethylbenzaldehyde (37 g, 0.27 moles), 80 mL of methanol, and 2.5 g of water. p-Toluenesulfonic acid (3 g) was then added upon heating. The reaction then proceeded with increased temperature to reflux. Water was removed continuously from the Dean-Stark trap, and additional solvent was added as needed. After 6 hours, the reaction mixture was cooled and neutralized with 3.3 g of KOH in methanol (40 mL). 500 mL of water was then added, and the cyclohexane layer was then removed azeotropically, producing a residual white solid which was then filtered. The white solid was then washed with water, hot methanol, and oven dried. The product was produced in 91% yield, comprising about 63% of 1,3-O-(3,4-dichlorobenzylidene):2,4-O-(3,4-dimethylbenzylidene) sorbitol and 1,3-O-(3,4-dimethylbenzylidene):2,4-O-(3,4-dichlorobenzylidene) sorbitol, 25% of 1,3:2,4-bis(3,4-dimethylbenzylidene) sorbitol, and the remainder (12%) of 1,3:2,4-bis(3,4-dichlorobenzylidene) sorbitol (as determined through Infrared Spectroscopy, Gas Chromatography/Mass Spectrometry, $^1$H NMR, and $C^{13}$ NMR, all collectively hereinafter referred to as "standard analyses"). DSC analysis of the solid @ 20° C./min showed melting transitions at about 266–268° C.

EXAMPLE 2

Preparation of Asymmetric 3,4-dichlorobenzylidene/6-tetrahydronaphthylidene sorbitol A one liter four-necked cylindrical shaped reaction flask equipped with a Dean-Stark trap, condenser, thermometer, nitrogen inlet, and a mechanical stirrer was charged with 42.00 g of sorbitol (0.2306 moles), 700 mL of cyclohexane, 40.3 g of 3,4-dichlorobenzaldehyde (0.2306 moles), 36.9 of 6-formyltetralin (0.2306 moles), 3.00 g of p-toluenesulfonic acid, and 100 mL of methanol. The reaction was stirred and heated under reflux with removal of water through the Dean Stark trap. The reaction became very thick and additional solvent was added as needed. After about six hours, the reaction was cooled, neutralized with potassium hydroxide, and filtered. The wet cake was washed thoroughly with water and methanol, dried in a vacuum oven at 110° C. to give 72.6 g (61%) of a white powder. The DBS purity was about 99% as judged by GC. Standard analyses of the material indicated that it consisted of a mixture of 1,3-O-(3,4-dichlorobenzylidene):2,4-O-(6-tetrahydronaphthylidene) sorbitol and 1,3-O-(6-tetrahydronapthylidene):2,4-O-(3,4-dichlorobenzylidene) sorbitol (60.4%), 1,3:2,4-bis(6-tetrahydronaphthylidene) sorbitol (25%), and 1,3:2,4-bis(3,4-dichlorobenzylidene) sorbitol (12.6%). DSC analysis of the solid @ 20° C./min showed melting transitions at 255.8–256.7° C.

EXAMPLE 3

Preparation of Asymmetric 3,4-Difluoro/3,4-Dimethyl [50/50] DBS

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 700 mL of cyclohexane, 40.4 g of 3,4-difluorobenzaldehyde (0.2306 moles), 30.93 g of 3,4-dimethylbenzaldehyde (0.2306 moles), 3.00 g of p-toluenesulfonic acid, and 100 mL of methanol. The reaction was stirred and heated under reflux with removal of water through the Dean Stark trap. The reaction became very thick and additional solvent was added as needed. After about six hours, the reaction was cooled, neutralized with potassium hydroxide, and filtered. The wet cake was washed thoroughly with water and methanol, dried in a vacuum oven at 110° C. to give 78.29 g of a white powder. The purity was about 95% as judged by GC. Standard analyses of the material indicated that it consisted of a mixture of 1,3-O-(3,4-difluorobenzylidene):2,4-O-(3,4-dimethylbenzylidene) sorbitol and 1,3-O-(3,4-dimethylbenzylidene):2,4-O-(3,4-difluorobenzylidene) sorbitol (60.7%), 1,3:2,4-bis(3,4-dimethylbenzylidene) sorbitol (21.2%), and 1,3:2,4-bis(3,4-difluorobenzylidene) sorbitol (18.0%). DSC analysis of the solid @ 20° C./min showed a melting transition range of 226–236° C.

EXAMPLE 4

Production of 3,4-dimethoxy/3,4-dichloro [50/50] DBS

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 700 mL of cyclohexane, 3,4-dimethoxybenzaldehyde (38 g, 0.2306 moles), 3,4-dichlorobenzaldehyde (40 g, 0.2306 moles), 3.00 g of p-toluenesulfonic acid, and 210 mL of methanol. The reaction was stirred and heated under reflux with removal of water through the Dean Stark trap. The reaction became very thick and additional solvent was added as needed. After about six hours, the reaction was cooled, neutralized with potassium hydroxide, and filtered. The wet cake was washed thoroughly with water and cyclohexane, dried in a vacuum oven at 110° C. to give a white solid. Standard analyses of the material indicated that it consisted of about 52% of a mixture of 1,3-O-(3,4-dimethoxybenzylidene):2,4-O-(3,4-dichlorobenzylidene) sorbitol and 1,3-O-(3,4-dichlorobenzylidene):2,4-O-(3,4-dimethoxybenzylidene) sorbitol, and about 48% of 1,3:2,4-bis(3,4-dichlorobenzylidene) sorbitol, with no 3,4-dimethoxy DBS present. DSC analysis of the solid @ 20° C./min showed a melting transition range of 250–252° C.

EXAMPLE 5

Production of 3,4-dichlorobenzylidene/5-indanylidene [50/50] DBS

A one liter four-necked cylindrical shaped reaction flask equipped with a Dean-Stark trap, condenser, thermometer, nitrogen inlet, and a mechanical stirrer was charged with sorbitol (25.2 g, 0.138 moles), ice (23.6 g), and concentrated HCl (44.5 g). After fifteen minutes of stirring, 24.2 g (0.139 moles) of 3,4-dichlorobenzaldehyde and 5-formylindan (18.5 g, 0.138 moles) were added as a mixture. A solution of cold water (200 mL) and KOH (72.0 g) was then added after 48 hours of further stirring. The resultant solids were then filtered, washed in hot water and hot methanol and vacuum-dried. Standard analyses showed the product to be 98% pure in asymmetrical diacetals. The product distribution could not be accurately determined due to the apparent similar volatility of the analytes. DSC analysis of the solid @ 20° C./min showed a melting transition range of 256–258° C.

EXAMPLE 6

Production of 4-nitro/3,4-dimethyl [50/50] DBS

A one liter four-necked cylindrical shaped reaction flask equipped with a Dean-Stark trap, condenser, thermometer, nitrogen inlet, and a mechanical stirrer was charged with 25.4 g of D-sorbitol (0.139 moles), 15.4 g of water, and 34.8 g of concentrated HCl with stirring. Subsequently, 20.8 g (0.138 moles) of 4-nitrobenzaldehyde and 18.5 g (0.138 moles) of 3,4-dimethylbenzaldehyde were charged as a mixture and added to the homogenous mixture. A solid block of material formed within one hour of reaction and stirring was impossible. 200 mL of cold water and 56.2 g of KOH were then added permitting filtering of the resultant solids. The yellow filtrate measured a pH of about 14. The remaining solids were then washed with 300 mL of hot water and then 200 mL of hot methanol yielding a tan solid of 4-nitro/3,4-dimethyl asymmetric DBS (46.5 g) mixture. The components of this mixture were determined to be (through standard analyses) 15.1% 3,4-dimethyldibenzylidene sorbitol, 18.9% 4-nitrodibenzylidene sorbitol, and 62.4% mixed asymmetries [1,3-O-(4-nitrobenzylidene):2,4-O-(3,4-dimethylbenzylidene) sorbitol and 1,3-O-(3,4-dimethylbenzylidene:2,4-O-(4-nitrobenzylidene) sorbitol]. The melting transition was found to be 224–227° C. by DSC analysis.

EXAMPLE 7

Production of asymmetric 4-nitro/3,4-methylenedioxy DBS

A one liter four-necked cylindrical shaped reaction flask equipped with a Dean-Stark trap, condenser, thermometer, nitrogen inlet, and a mechanical stirrer was charged with 25.2 g of sorbitol (0.138 mole) and 34.7 g of concentrated HCl. Subsequently, 21.0 g (0.139 moles) of 4-nitrobenzaldehyde and 20.9 g (0.139 moles) of piperonal (3,4-methylenedioxybenzaldehyde) were charged as a mixture and added to the homogenous mixture. After two hours the reaction mixture turned yellow and some began to adhere to the sides of the flask. After seven more hours of such mixing, 200 mL of cold water and 56.8 g of KOH were then added and stirred for another 8 hours. Subsequently, the resultant solids were then collected, washed (in boiling water and boiling methanol) and filtered. The yellow-green filtrate measured a pH of about 14. This procedure yielded about 28 g of the 4-nitro/3,4-methylenedioxy asymmetric DBS mixture. The components of this mixture were determined to be (through standard analyses) 9.06% bis(3,4-methylenedioxybenzylidene) sorbitol, 16.63% bis(4-nitrobenzylidene) sorbitol, and 74.31% mixed asymmetries [1,3-O-(4-nitrobenzylidene):2,4-O-(3,4-methylenedioxybenzylidene) sorbitol and 1,3-O-(3,4-methylenedioxybenzylidene):2,4-O-(4-nitrobenzylidene) sorbitol]. The melting transition was found to be 194–204° C. by DSC analysis.

EXAMPLE 8

Preparation of Asymmetric 3,4-Dichloro/3,4-Dimethyl DBX

A one liter four-necked cylindrical shaped reaction flask equipped with a Dean-Stark trap, condenser, thermometer, nitrogen inlet, and a mechanical stirrer was charged with 40.00 g of xylitol (0.263 moles), 600 mL of cyclohexane, 46 g of 3,4-dichlorobenzaldehyde (0.263 moles), 35.2 g of 3,4-dimethylbenzaldehyde (0.263 moles), 3.00 g of p-toluenesulfonic acid, and 100 mL of methanol. The reaction was stirred and heated under reflux with removal of water through the Dean Stark trap. The reaction became very thick and additional solvent was added as needed. After about six hours, the reaction was cooled, neutralized with potassium hydroxide, and filtered. The wet cake was washed thoroughly with water and cyclohexane and dried in a vacuum oven at 110° C. to give 108.9 g (98%) of asymmetric 3,4-dichloro/3,4-dimethyl DBX. The purity was determined to be 98% through gas chromatography analysis. Standard analyses of the material indicated that it consisted of a mixture of 1,3-O-(3,4-dichlorobenzylidene):2,4-O-(3,4-dimethylbenzylidene) xylitol and 1,3-0-(3,4-dimethylbenzylidene):2,4-O-(3,4-dichlorobenzylidene) xylitol (78.7%), 1,3:2,4-bis(3,4-dimethylbenzylidene) xylitol (14.7%), and 1,3:2,4-bis(3,4-dichlorobenzylidene) xylitol (6.6%). The melting transition, as determined by melting point apparatus at a heating rate of 2° C./minute, was found to be 248.2–251.9° C.

Polyolefin Formation and Testing

One kilogram batches of target polypropylene were produced in accordance with the following table:

| POLYPROPYLENE COMPOSITION TABLE | |
| --- | --- |
| Component | Amount |
| Polypropylene random copolymer flake (3% ethylene) (MF = 12) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Diacetal (and diacetal compositions) | as noted |

The base resin (random copolymer, hereinafter "RCP") and all additives were weighed and then blended in a Welex mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The barrel molder was set at a temperature anywhere between 190 and 260° C., with a range of 210 to 240° C. more preferred, and most preferably from about 220 to 230° C. The plaques had dimensions of about 51 mm X 76 mm X 1.27 mm, and were made in a mold having a mirror finish. The mold cooling circulating water was controlled at a temperature of about 25° C.

The haze values were measured by ASTM Standard Test Method D1003-61 "Standard Test Method for Haze and Luminous Transmittance of Transparent Plastics" using a BYK Gardner XL-211 Hazemeter. Nucleation capabilities were measured as polymer recrystallization temperatures (which indicate the rate of polymer formation provided by the presence of the nucleating additive) by melting the target plaques and recording the temperature at which polymer re-formation occurs. An asterisk (*) denotes no measurements were taken.

EXPERIMENTAL TABLE 1

| Test Plaque | (DBS Ex. # above) | Amount added (ppm) | Haze (%) | $T_c$ (° C.) |
|---|---|---|---|---|
| 1 | 1 | 1000 | 37.9 | * |
| 2 | 1 | 1500 | 16.3 | * |
| 3 | 1 | 2000 | 9.1 | * |
| 4 | 1 | 2500 | 7.1 | * |
| 5 | 1 | 3000 | 6.5 | 113.1 |
| 6 | 1 | 3500 | 6.4 | 113.4 |
| 7 | 1 | 5000 | 6.3 | 113.3 |
| 8 | 2 | 1500 | 34.5 | * |
| 9 | 2 | 3500 | 11.1 | 110.7 |
| 10 | 3 | 1500 | 14.3 | * |
| 11 | 3 | 2500 | 9.0 | * |
| 12 | 3 | 3500 | 7.1 | 112.6 |
| 13 | 4 | 1500 | 29.5 | * |
| 14 | 4 | 3500 | 12.1 | 108.9 |
| 15 | 5 | 2500 | 11.9 | * |
| 16 | 5 | 3500 | 12.3 | 111.3 |
| 17 | 6 | 1500 | 14.2 | * |
| 18 | 6 | 3500 | 10.4 | 109.9 |
| 19 | 7 | 1000 | 22.0 | * |
| 20 | 7 | 1500 | 26.5 | 105.8 |
| 21 | 8 | 3500 | 48.0 | 103.0 |

Thus, the dipolar asymmetric DBS derivatives (within reaction product mixtures), exhibited favorable haze measurements and recrystallization temperatures in polypropylene plaques.

Gel Formation and Testing

Solid gels were also produced comprising the inventive alditol derivatives through recognized, simple methods. In particular, specific organic solvents were combined with the additives in certain concentrations and mixed thoroughly for between 5 and 120 minutes at an elevated temperature between about 100° F. (77° C.) and 300° F. (149° C.), preferably about 110° C., or at a temperature approaching, but not exceeding, the boiling point of the selected solvent (or solvents) to be gelled. The resultant solution was then poured into a mold and allowed to cool to room temperature to produce a gel stick. The solvents listed below are not intended to be exhaustive as to the potential types which may be utilized to form gels with the inventive alditol derivatives, and thus are merely listed as preferred solvents for such purposes. The examples below were analyzed empirically and by touch to determine if a gel actually formed and the hardness properties as well as any formed gels.

EXPERIMENTAL TABLE 2

| Ex. No. | Solvent | Additive - from Example # above | DBS Conc. (weight %) | Gel Formation (Y/N) | Gel Character (Hard/Soft) |
|---|---|---|---|---|---|
| 22 | 1,2-Propanediol | 1 | 1 | Y | Soft |
| 23 | 1,2-Propanediol | 1 | 3 | Y | Hard |
| 24 | 2-Chlorotoluene | 1 | 1 | Y | Hard |
| 25 | 2-Chlorotoluene | 1 | 3 | Y | Hard |
| 26 | 1,2-Propanediol | 8 | 1 | Y | Soft |
| 27 | 1,2-Propanediol | 8 | 3 | Y | Hard |
| 28 | 2-Chlorotoluene | 8 | 1 | Y | Hard |
| 29 | 2-Chlorotoluene | 8 | 3 | Y | Hard |

Thus, the inventive asymmetric fluorine or fluorinated alditol derivatives provide excellent gelling capabilities for solvents, depending on their concentration within the target solvents.

There are, of course, many alternative embodiments and modifications of the present invention which are to be included within the spirit and scope of the following claims.

What is claimed is:

1. A reaction product mixture comprising at least two isomeric compounds meeting the following description: an asymmetric alditol di-acetal compound comprising at least two arylidene components wherein one of said arylidene components possesses either a single nitro pendant group or at least two electron withdrawing pendant groups and the other arylidene component must comprise at least two electron donating pendant groups; wherein said reaction product mixture includes at least one other reaction product, wherein said at least one other reaction product is a symmetrical alditol compound.

2. A reaction product mixture comprising at least two isomeric compounds meeting the following description: at least one alditol di-acetal compound conforming with the Formula (I):

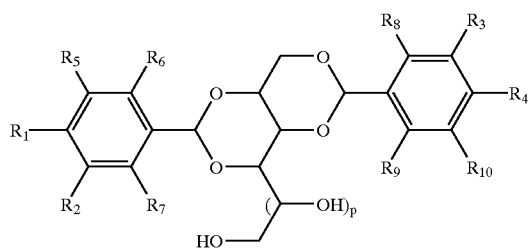

(I)

wherein p is 0 or 1, $R_5$, $R_6$, $R_7$, $R_8$, $R_9$, and $R_{10}$ are each the same or different and are electron donating groups, selected from hydrogen, lower alkyl groups containing 1–4 carbon atoms, lower alkoxy groups, or electron withdrawing groups, selected from nitro, fluorine, chlorine, bromine, and iodine; $R_1$, $R_2$, $R_3$, and $R_4$ are the same or different and are selected from hydrogen, lower alkyl groups containing 1–4 carbon atoms, lower alkoxy groups, indan, tetralin, benzyl, substituted benzyl, or any two are combined to form a cyclic moiety, nitro, fluorine, chlorine, bromine and iodine; with the first proviso that if one of said $R_1$, $R_2$, $R_3$, or $R_4$ groups is nitro, then no other nitro groups are present anywhere on the compound; with a second proviso that, unless a single nitro group is present, at least two electron withdrawing groups must be present and must be present as either the pair of $R_1$ and $R_2$ or the pair of $R_3$ and $R_4$ such that if one pair comprises such electron withdrawing groups, the other pair must comprise electron donating groups and the same ring system comprising such electron donating groups must not comprise any electron withdrawing groups; wherein said reaction product mixture includes at least one other reaction product, wherein said at least one other reaction product is a symmetrical alditol compound.

* * * * *